US009717512B2

(12) United States Patent
Schmalzried et al.

(10) Patent No.: US 9,717,512 B2
(45) Date of Patent: Aug. 1, 2017

(54) PROGRAMMABLE FEMORAL PIN GUIDE (71) Applicant: Howmedica Osteonics Corp., Mahwah, NJ (US)

(72) Inventors: Thomas Schmalzried, Rolling Hills, CA (US); Kimberly Sepulveda, Newbury Park, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 832 days.

(21) Appl. No.: 14/087,674

(22) Filed: Nov. 22, 2013

(65) Prior Publication Data
US 2014/0148809 A1 May 29, 2014

Related U.S. Application Data (60) Provisional application No. 61/764,665, filed on Feb. 14, 2013, provisional application No. 61/729,768, filed on Nov. 26, 2012.

(51) Int. Cl.
A61B 17/17 (2006.01)
A61B 17/15 (2006.01)

(52) U.S. Cl.
CPC ........ A61B 17/1764 (2013.01); A61B 17/155 (2013.01)

(58) Field of Classification Search
CPC .......................... A61B 17/155; A61B 17/1764
See application file for complete search history.

(56) References Cited

U.S. PATENT DOCUMENTS

| 5,098,383 | A |  | 3/1992 | Hemmy et al. |
| 5,624,444 | A |  | 4/1997 | Wixon et al. |
| 5,662,656 | A |  | 9/1997 | White |
| 5,688,282 | A |  | 11/1997 | Baron et al. |
| 6,013,081 | A | * | 1/2000 | Burkinshaw ......... A61B 17/155 606/102 |
| 7,621,920 | B2 |  | 11/2009 | Claypool et al. |

(Continued)

FOREIGN PATENT DOCUMENTS

WO 2011141723 A1 11/2011

OTHER PUBLICATIONS

International Search Report and Written Opinion for Application No. PCT/US2013/071502 dated Feb. 13, 2014.

Primary Examiner — Nicholas Woodall
(74) Attorney, Agent, or Firm — Lerner, David, Littenberg, Krumholz & Mentlik, LLP (57) ABSTRACT A guide for use prior to, or concurrently with, resecting a portion of a patient's bone includes a body, an anterior adjustment member, at least one posterior adjustment foot, at least one adjustable condylar alignment pin, an adjustable anterior arm, and means to direct guide pins into the femur. The body has multiple apertures configured to accept pins. The anterior adjustment member is coupled to the body and moves toward/away from the femur and contacts an anterior portion of the femur. The posterior adjustment foot is coupled to the body and moves toward/away from the femur and contacts a posterior portion of the femur. The anterior arm is coupled to the anterior adjustment member and is configured to contact the femur proximal of the anterior adjustment member. The rotation arm is coupled to the body and provides guides to drill into the femur.

19 Claims, 7 Drawing Sheets (56) References Cited

U.S. PATENT DOCUMENTS

| | | |
|---|---|---|
| 7,641,660 B2 | 1/2010 | Lakin et al. |
| 7,794,467 B2 | 9/2010 | McGinley et al. |
| 2002/0156361 A1 | 10/2002 | Popowski et al. |
| 2005/0209600 A1 | 9/2005 | Fencl et al. |
| 2006/0122617 A1 | 6/2006 | Lavallee et al. |
| 2008/0195109 A1 | 8/2008 | Hunter et al. |
| 2010/0191244 A1 | 7/2010 | White et al. |
| 2010/0211077 A1 | 8/2010 | Couture et al. |
| 2010/0241126 A1 | 9/2010 | Ghijselings |
| 2010/0256479 A1 | 10/2010 | Park et al. |
| 2010/0268240 A1 | 10/2010 | McGinley et al. |
| 2011/0106095 A1 | 5/2011 | Cross et al. |
| 2011/0214279 A1 | 9/2011 | Park et al. |
| 2011/0245835 A1 | 10/2011 | Dodds et al. |

\* cited by examiner

PROGRAMMABLE FEMORAL PIN GUIDE

CROSS-REFERENCE

The present application claims the benefit of the filing date of U.S. Provisional Application No. 61/729,768, filed Nov. 26, 2012 and U.S. Provisional Application No. 61/764,665, filed Feb. 14, 2013, both entitled PROGRAMMABLE FEMORAL PIN GUIDE, the disclosures of which are hereby incorporated herein by reference.

FIELD OF THE TECHNOLOGY

The present invention relates to systems and methods for planning and performing arthroplasty. More specifically, the present invention relates to adjustable/programmable pin guides for planning and performing knee arthroplasty.

BACKGROUND OF THE INVENTION

Over time and through repeated use, joints can become damaged or worn. For example, repetitive stress and strain on joints (e.g., strenuous activity, traumatic events, and certain diseases such as infection and rheumatoid arthritis) can cause the surfaces of the joint to wear out or otherwise break down. Such degeneration of the joint surfaces can result in pain, swelling, stiffness, deformity, and decreased mobility.

Arthroplasty procedures can be performed to repair damaged joints. During an arthroplasty procedure, an arthritic or otherwise dysfunctional joint can be remodeled or realigned, or a prosthesis can be implanted into the damaged region. Arthroplasty procedures may take place in any of a number of different joints in the body, such as a knee, a hip, a shoulder, or an elbow.

One type of arthroplasty procedure is a total knee arthroplasty ("TKA"), in which the articulating surfaces of a knee joint are replaced or resurfaced with prosthetic implants. The knee joint may have, for example, been worn out due to degenerative arthritis, been injured from trauma or infection, or been deteriorated due to another joint disease. During a TKA procedure, the articulating surfaces of the distal femur may be resurfaced or removed and replaced with a femoral component, and the articulating surfaces of the proximal tibia may be resurfaced or removed and replaced with a tibial component. The surfaces of the femoral and tibial components are configured to articulate with each other. In some TKA procedures, the articular surface of the patella may be replaced with a patellar component, depending on the condition of the patella.

The prosthetic implants are firmly attached to the adjacent bones and have smooth articulating surfaces to allow pain-free motion. Prior to implantation of an implant, the damaged region is prepared to receive the implant. For example, in a knee arthroplasty procedure, the distal femur and/or proximal tibia, may be prepared (e.g., cut, drilled, reamed) to provide one or more surfaces that can mate with the implant and thereby physically support the implant.

Generally, when preparing the femur for arthroplasty, up to five cuts may be made on the femur, including a distal cut, an anterior cut, a posterior cut, an anterior chamfer cut and a posterior chamfer cut. Usually, a first device is used to make the distal cut. A second device, often called a 4-in-1 cutting block, is used to make the remaining four cuts. The accuracy of these cuts, including the position and orientation thereof, is an important factor in the accuracy of the alignment of implants that are fixed to the bone. A one- to two-millimeter translational misalignment, or a one- to two-degree angular or rotational misalignment, may adversely affect the outcome of the TKA procedure. For example, implant misalignment may result in intolerable post-surgery pain, and also may prevent the patient from having full knee extension and/or full and stable knee flexion.

BRIEF SUMMARY OF THE INVENTION

In one embodiment, an adjustable femoral pin guide includes a body with a plurality of apertures, at least one of the apertures configured to receive a pin and at least one pin being configured to contact the femur. The guide includes an anterior adjustment member configured to be coupled to an anterior portion of the body and being configured to move toward or away from the femur and further being adapted to contact an anterior portion of the femur. The guide further includes at least one posterior adjustment foot configured to be coupled to a posterior portion of the body and being configured to move toward or away from the femur and further being adapted to contact a posterior portion of the femur. The guide may additionally include an anterior arm configured to be coupled to a proximal portion of the anterior adjustment member, the anterior arm including a bone contacting portion configured to contact the femur proximal of the anterior adjustment member.

The at least one posterior adjustment foot may comprise a medial posterior adjustment foot and a lateral posterior adjustment foot. The medial posterior adjustment foot may be configured to be coupled with a medial extension of the body and further be configured to contact the medial condyle on a posterior portion thereof. The lateral posterior adjustment foot may be configured to be coupled with a lateral extension of the body and further be configured to contact the lateral condyle on a posterior portion thereof.

The guide may include a plurality of apertures in the medial extension and a plurality of apertures in the medial posterior adjustment foot, the apertures in the medial extension configured to align with the apertures in the medial posterior adjustment foot and to accept a medial foot fastener therethrough. The guide may also include a plurality of apertures in the lateral extension and a plurality of apertures in the lateral posterior adjustment foot, the apertures in the lateral extension configured to align with the apertures in the lateral posterior adjustment foot and to accept a lateral foot fastener therethrough.

The plurality of apertures in the medial extension and the plurality of apertures in the medial posterior adjustment foot may be arranged such that the medial posterior adjustment foot is capable of being fastened to the medial extension in at least two discrete positions in a medial/lateral direction and in at least two discrete positions in a anterior/posterior direction. The plurality of apertures in the lateral extension and the plurality of apertures in the lateral posterior adjustment foot may be arranged such that the lateral posterior adjustment foot is capable of being fastened to the lateral extension in at least two discrete positions in the medial/lateral direction and in at least two discrete positions in the anterior/posterior direction.

The anterior adjustment member may further include a first extension including a plurality of apertures, each of the plurality of apertures in the first extension configured to align with at least one of the plurality of apertures in the body and to accept a first extension fastener therethrough. The plurality of apertures in the first extension and the plurality of apertures in the body may be arranged such that the first extension is capable of being fastened to the body in at least two discrete positions in an anterior/posterior direction.

The anterior adjustment member may further include a second extension including a plurality of apertures, each of the plurality of apertures in the second extension configured to align with at least one of the plurality of apertures in the body and to accept a second extension fastener therethrough. The plurality of apertures in the second extension and the plurality of apertures in the body may be arranged such that the second extension is capable of being fastened to the body in at least two discrete positions in an anterior/posterior direction.

The anterior adjustment member may further include a slot or aperture extending from an anterior portion of the anterior adjustment member to a posterior portion of the anterior adjustment member and may be configured to accept a cutting instrument or other tool therethrough. Alternately, the slot or aperture may be entirely omitted from the anterior adjustment member. The anterior adjustment member may include at least two drill guide apertures in the anterior adjustment member configured to guide a drill. The drill guide apertures may correspond with pin apertures of a separate distal resection cutting guide.

The anterior adjustment member may further include a plurality of posterior apertures, each of the plurality of proximal apertures configured to align with at least one of a plurality of apertures in the anterior arm and capable of accepting an anterior arm fastener therethrough. The plurality of posterior apertures and the plurality of apertures in the anterior arm may be arranged such that the anterior arm is capable of being fastened to the anterior adjustment member in at least two discrete positions in a medial/lateral direction and in at least two discrete positions in a proximal/distal direction. The anterior arm may also be capable of being positioned in at least two discrete positions in the anterior/posterior direction with respect to the anterior adjustment member.

The guide may further include a rotation arm configured to couple with a distal portion of the body, the rotation arm including at least two guide members, each guide member being configured to accept at least one of a pin or a drill. The body may include a rotation arm recess with a medial side, a lateral side, and an anterior side, the rotation arm recess being configured to accept at least a portion of the rotation arm. The anterior side of the rotation arm recess may include a textured surface and an anterior portion of the rotation arm may include a textured surface, the textured surface of the recess configured to contact the textured surface of the rotation arm when the rotation arm is coupled to the body.

In an embodiment of the invention, a method of performing surgery on at least a portion of a bone of a patient includes the steps of imaging the bone, determining multiple guide coordinates based on the bone image, and providing an adjustable guide including a body having a plurality of apertures, an anterior adjustment member, and at least one posterior adjustment foot. The adjustable guide may also include an anterior arm. A further step includes coupling at least one posterior adjustment foot to the body by inserting at least one adjustment foot pin through a first of a plurality of body apertures and further into a first of a plurality of posterior adjustment foot apertures, wherein the first of the plurality of body apertures and the first of the plurality of posterior adjustment foot apertures are chosen based on the determined guide coordinates for that bone. Additional steps may include contacting the at least one posterior adjustment foot to a posterior portion of the bone, inserting an intercondylar notch pin through an intercondylar notch pin aperture in the body, and translating the body medially or laterally until the intercondylar notch pin contacts a medial side of a lateral condyle or a lateral side of a medial condyle. Still further steps may include inserting a medial condyle pin through a medial condyle aperture in the body, inserting a lateral condyle pin through a lateral condyle aperture in the body, contacting the medial condyle pin with the medial condyle, and contacting the lateral condyle pin with the lateral condyle.

The method may also include the steps of contacting a posterior side of the anterior adjustment member to an anterior portion of the bone and inserting an anterior adjustment member pin through a second of the plurality of body apertures and further into a first of a plurality of anterior adjustment member apertures to couple the anterior adjustment member to the body, wherein the second of the plurality of body apertures and the first of the plurality of anterior adjustment member apertures are chosen based on the determined guide coordinates.

The method may further include the steps of inserting the anterior arm into the anterior adjustment member, contacting the anterior arm with the bone, and inserting an anterior arm pin through a second of the plurality of anterior adjustment member apertures and further into a first of a plurality of anterior arm apertures, wherein the second of the plurality of anterior adjustment member apertures and the first of the plurality of anterior arm apertures are chosen based on the determined guide coordinates.

The method may still further include the steps of drilling holes into the bone using drill guide apertures in the anterior adjustment member, inserting distal resection guide pins into the holes drilled into the bone, inserting a cutting device into a cutting slot of a distal resection guide coupled to the bone by the distal resection guide pins, and resecting a distal portion of the femur. The distal resection guide may be the anterior adjustment member, or the distal resection guide may a device entirely separate from the anterior adjustment member.

The method may yet further include the steps of providing a rotation arm configured to couple to a distal side of the body, the rotation arm including a medial guide arm and a lateral guide arm, coupling the rotation arm to the body, inserting a drill through the medial guide arm and drilling a hole in the medial condyle, and inserting a drill through the lateral guide arm and drilling a hole in the lateral condyle.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Prior to making the distal cut in a TKA procedure, a femoral cutting guide has to be oriented correctly with respect to the distal femur in order to achieve a desired limb alignment for that patient. In order to accurately position the cutting guide, alignment instruments may be used to place guide pins in the bone to accommodate one or more apertures of the cutting guide for orienting and stabilizing the cutting guide in a particular position. Guide pin placement for the distal femoral cut is important because the resulting distal femoral cut is generally used to reference another guide (e.g. a 4-in-1 guide) for the other resections needed to prepare the bone to receive a femoral implant (e.g. the anterior, posterior, and chamfer cuts). Current surgical procedures generally accomplish this task in one of two ways.

Traditional procedures utilize preoperative x-rays, anatomical landmarks found intraoperatively, multiple instruments, and surgeon experience and judgment to select the appropriate implant size and intended three-dimensional position including: varus/valgus angle, flexion/extension angle, distal resection level, anterior and posterior resection levels, and internal/external rotation orientation.

Patient-specific procedures may also be utilized. These procedures generally use three-dimensional imaging software and rapid manufacturing technology to create a unique, disposable femoral guide for each patient. The size and position of the femoral guide on the bone are determined preoperatively. These patient-specific femoral guides may be used in making the distal cut as well as guide the placement of pins, which may later be used in conjunction with another device for making the remaining cuts. Generally, these patient-specific guides are manufactured for single use.

Referring to the figures, there is shown an embodiment of an adjustable patient-specific pin guide for the distal femur of the present invention designated generally by reference numeral 10. The pin guide 10 may be patient-specific in that it is programmable to a particular patient's anatomy. However, the guide 10 may be reusable as it may be reprogrammed for a specific patient's anatomy prior to each use.

Generally, prior to patient-specific arthroplasty, a patient undergoes imaging of the knee, such as multi-plane x-rays, by MRI or other imaging techniques. Data obtained from imaging may be manipulated to convert the scans into a three-dimensional model of the knee. Based on the three-dimensional model, the size and intended position of the implant or implants are incorporated into a preoperative plan. Such systems are more fully described in U.S. Patent Publication Nos. 2011/0214279 and 2010/0256479, the entire contents of which are hereby both incorporated by reference herein in their entireties. The surgeon reviews the preoperative plan and makes changes if he sees fit. In traditional patient-specific procedures, after the surgeon's review and approval, a disposable guide is first manufactured based on the imaging data and preoperative plan and is then sent to the surgeon to guide the distal cut and pin placement during the operation. As is described in the current disclosure, the same or similar imaging data can be used in conjunction with a programmable femoral pin guide 10 to guide the surgeon without the need for the manufacturing and shipping steps of traditional patient-specific procedures. While both techniques are patient-specific, the programmable pin guide 10 does not need to be manufactured for each use, as it may be reprogrammed to suit the anatomy of a particular patient, and later may be reprogrammed for a different patient's anatomy in a later surgery. As such, the femoral pin guide 10 described herein can reduce time and cost associated with producing traditional patient-specific guides.

Generally, the femoral pin guide 10 can fit a variety of patient anatomies by having several moving parts that can be adjusted to contact anatomical landmarks on the distal femur. Software may determine the settings needed to position the moving parts for an exact fit to the distal femur in order to achieve the cuts for the agreed upon three dimensional position for the femoral implant.

In the current disclosure, reference is made to directions with respect to the femur 20 and the femoral pin guide 10, including proximal, distal, anterior, posterior, medial, and lateral. "Distal" refers to a location farther from the heart (toward the left in FIG. 1), and "proximal" refers to a location closer to the heart (toward the right in FIG. 1). "Anterior" refers to the front or face of the patient (toward the top in FIG. 1), while "posterior" refers to the rear or back of the patient (toward the bottom in FIG. 1). "Medial" refers to a position closer to the mid-line of the body, while "lateral" refers to a position farther away from the mid-line of the body. When using these directional terms with respect to the devices described herein, the directions apply to the device as if it were positioned on the patient as positioned in FIG. 1, unless otherwise noted.

Figure 1:
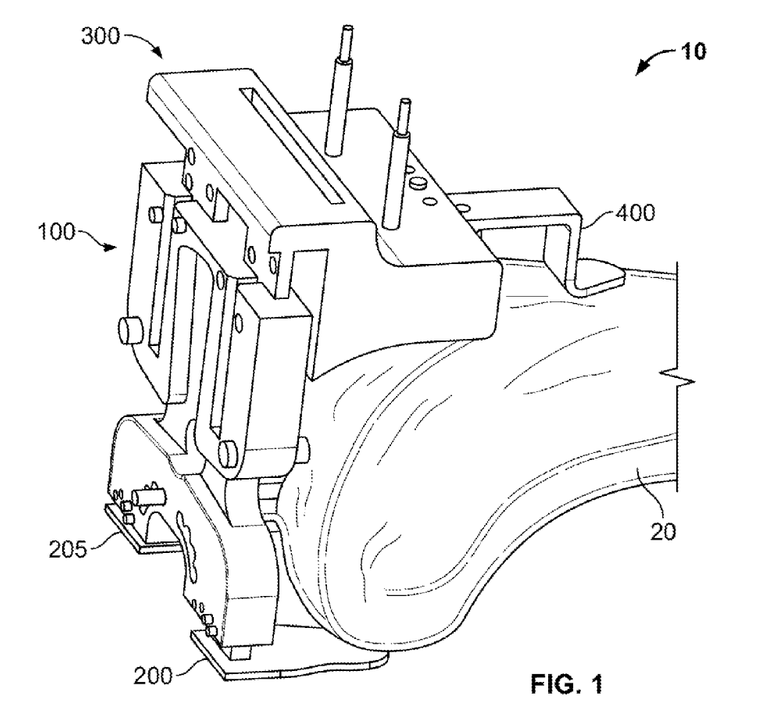
FIG. 1 is a perspective view of a femoral pin guide coupled to a femur according to an embodiment of the invention.

FIG. 1 illustrates the femoral pin guide 10 positioned on the distal end of the femur 20. The femoral pin guide generally includes a body 100, a medial posterior foot 200, a lateral posterior foot 205, an anterior translator 300, an anterior arm 400, and rotation arm 500 (rotation arm illustrated in FIGS. 6 and 14-15).

Figure 2:
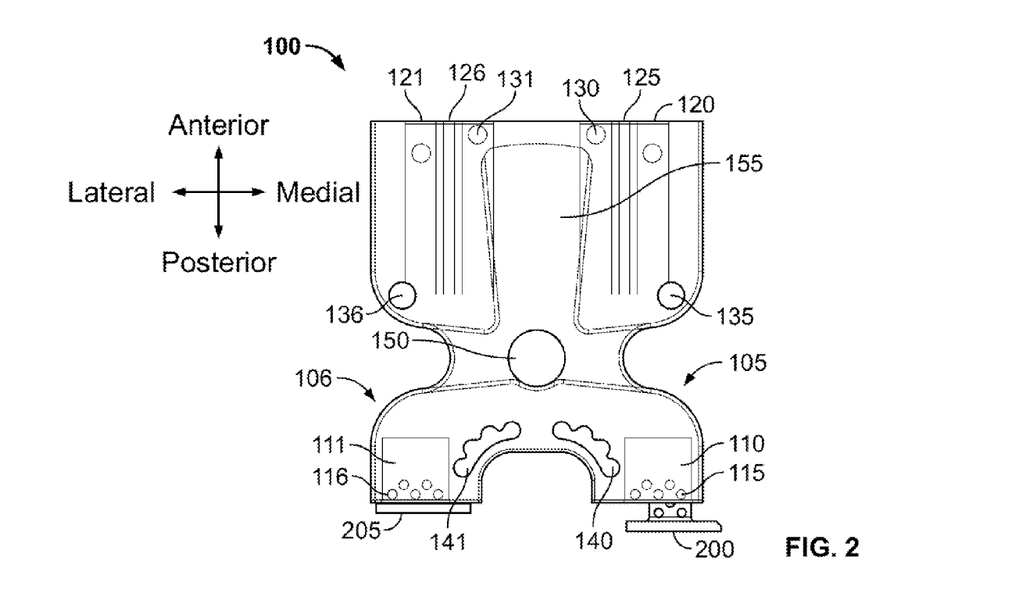
FIG. 2 is a front plan view in partial phantom lines of the body and posterior feet of the femoral pin guide of FIG. 1.

FIG. 2 illustrates body 100 with two posterior feet 200, 205 coupled to the posterior end of the body. Body 100 generally includes multiple apertures and/or slots that accept pins or other portions of the femoral pin guide 10. The material of the body 100 and other components described herein may be metal, plastic, or any other suitable material. The posterior end of the body 100 includes a medial extension 105 and a lateral extension 106. Medial extension 105 and lateral extension 106 each includes a slot 110, 111 open at the posterior end of the respective extension. Each extension 105, 106 also includes a plurality of apertures 115, 116 extending through the distal end of the respective extension and into the respective slot 110, 111. The slots 110, 111 function to accept the posterior feet 200, 205, while the apertures 115, 116 function to accept posterior foot pins 225 (illustrated in FIGS. 7, 10-14) to secure the posterior feet in their respective slots. The posterior feet 200, 205 are described in greater detail below with reference to FIG. 3.

Although the method of connecting different structures is generally described herein as a pin and aperture system, it should be understood that this is only one option. For example, posterior feet (200, 205) may include a ratchet feature on the feet corresponding to locking features in slots 110, 111 to allow for secured fixation in discrete increments without the use of pins and apertures. Similarly, the posterior feet may include cantilever features that are biased outward with protrusions that mate with discretely spaced recesses in slots 110, 111 for secured fixation in discrete increments. Friction would hold the components fixed relative to each other, until enough force was applied to overcome the friction and move the components relative to one another into the next discretely spaced position. Other mechanisms, such as a spring and ball detent system, are known in the art and the use of these alternate mechanisms would be a matter of design choice. These alternate mechanisms may provide for positioning at discrete spacing as opposed to being infinitely adjustable. These alternate mechanisms may also be used with respect to other components that described herein that use a pin and aperture mechanism for secured fixation. These other mechanisms may provide some benefit over the pin and aperture mechanism by reducing the number of moving parts (i.e. separate pin structures may not be required when using these alternate mechanisms).

The anterior end of the body 100 includes a medial slot 120 and a lateral slot 121. Slots 120, 121 are open at the anterior end of the body 100, extending posteriorly into the body. The distal end of the body 100 includes grooves 125, 126 that extend the length of the slots 120, 121 and are in communication with the slots. Each slot 120, 121 also includes a plurality of apertures 130, 131 extending from the distal end of the body 100 into the respective slot. The slots 120, 121 function to accept extensions 315, 320 of the anterior translator 300, while the apertures 130, 131 function to accept anterior translator pins 350 (illustrated in FIG. 11). The anterior translator 300 is described in greater detail below with reference to FIG. 4.

The body 100 additionally includes a medial aperture 135 and a lateral aperture 136. Each aperture 135, 136 extends through the body 100 from the distal surface to the proximal surface. Each aperture 135, 136 functions to accept medial and lateral condyle pins 605, 610 respectively, that can be inserted to a variable distal/proximal depth. The purpose of the condyle pins 605, 610 is valgus/varus guide positioning and is discussed in more detail below with reference to FIGS. 7-9. The body 100 further includes a plurality of medial apertures 140 and a plurality of lateral apertures 141 near the posterior end of the body. The apertures 140, 141 extend through the body 100 from the distal surface to the proximal surface. The apertures 140, 141 function to accept an intercondylar notch pin 600. The function of the intercondylar notch pin 600 is medial/lateral guide positioning and is discussed in more detail below with reference to FIGS. 7-9. The body 100 additionally includes a rotation arm aperture 150 extending through the body from the distal surface to the proximal surface. The rotation arm aperture 150 allows the rotation arm 500 to be coupled to the body 100. The body 100 additionally includes a rotation arm slot 155, shaped to receive the main body 505 of the rotation arm 500 and to provide boundaries for the rotation of the rotation arm. The function of the rotation arm 500 is internal/external rotational positioning of the distal guide pins and is discussed in greater detail below with reference to FIG. 6.

Figure 3:
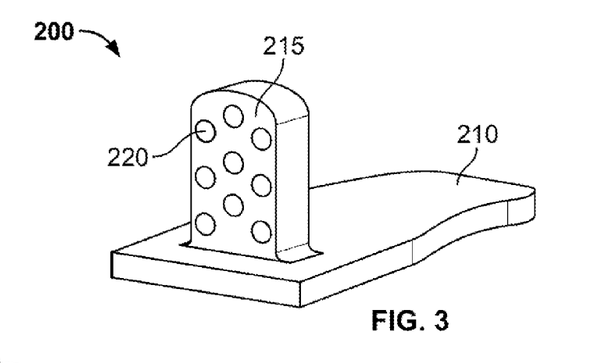
FIG. 3 is a perspective view of one of the posterior feet of FIG. 1.

FIG. 3 illustrates the medial posterior foot 200. Since the posterior feet 200, 205 are similar in structure, only the medial posterior foot will be described, it being understood that the structure also similarly applies to lateral posterior foot 205. Generally, medial posterior foot 200 includes a flat portion 210 and a foot extension 215 extending generally orthogonal to the flat portion. The anterior surface of the flat portion 210 functions to contact a posterior surface of a femoral condyle (medial condyle 30 or lateral condyle 40) to help secure the femoral pin guide 10 to the femur 20. The extension 215 is sized to be able to enter medial slot 110 of the body 100. The width of extension 215 is less than the width of medial slot 110 such that the medial posterior foot 200 can move medially and laterally while inside the medial slot. The posterior feet may have slightly different structure, for example each foot may flare in an opposite direction, such that each conforms to the respective condyle which it contacts. For example, the medial posterior foot 200, which contacts the medial condyle, may have a curvature for better contact with the medial condyle, while lateral posterior foot 205 may have slightly different curvature than the medial posterior foot 200 to provide for better contact with the lateral condyle. It is also envisioned in another embodiment that the feet 200, 205 are identical in structure, with no flaring or with identical flaring.

The extension 215 also includes a plurality of apertures 220 extending through the extension. These apertures 220 correspond to the apertures 115 in the medial extension 105 of the body 100. After inserting the extension 215 of the medial posterior foot 200 into the medial slot 110 of the body 100, one or more posterior foot pins 225 can be inserted through the apertures 115 in the medial extension 105 of the body and further into apertures 220 of the posterior foot extension to secure the medial posterior foot in a desired position. The numerous apertures 115 in the medial extension 105 and the numerous apertures 220 in the posterior foot extension 215 allow for the medial posterior foot 200 to be secured in multiple different positions. Specifically, the medial posterior foot 200 can be positioned in the anterior/posterior direction and in the medial/lateral direction. This configuration allows the posterior feet 200, 205 to be independently positioned in the medial/lateral and anterior/posterior directions, allowing adjustment to any size femur 20, even when distinct condylar sizes are present. The posterior feet 200, 205, once in place, provide stability to the femoral pin guide 10 and can provide the desired internal/external rotation orientation of the femoral pin guide.

Figure 4:
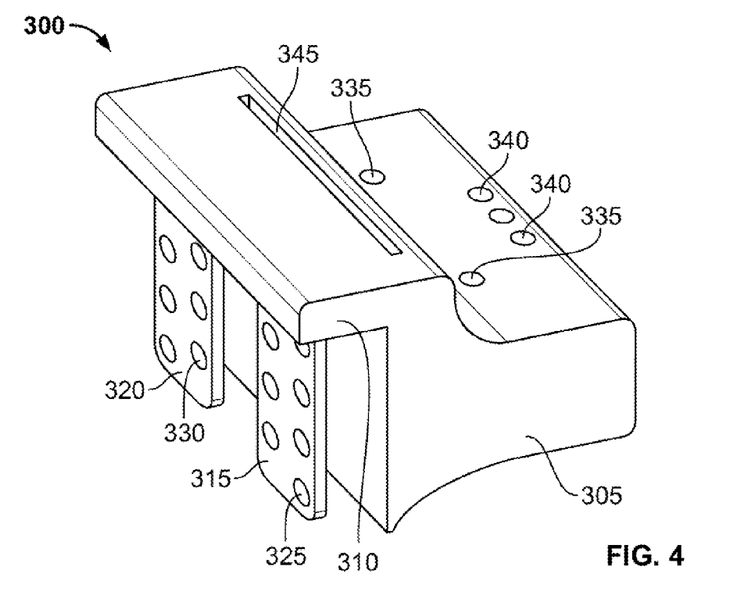
FIG. 4 is a perspective view of the anterior translator of FIG. 1.

Referring to FIG. 4, the anterior translator 300 is illustrated. The anterior translator generally includes a body 305 and a ledge 310 extending distally from the anterior portion of the body. Medial extension 315 and lateral extension 320 each extend posteriorly from the ledge 310. The medial extension 315 contains a plurality of apertures 325, and the lateral extension 320 includes a plurality of apertures 330. The medial extension 315 is dimensioned to slide into and fit in the medial slot 120 of the body 100, while the lateral extension 320 is dimensioned to slide into and fit in the lateral slot 121 of the body.

The grooves 125, 126 in the medial and lateral slots 120, 121 respectively, enable a surgeon or other user to visually determine how far the medial and lateral extensions 315, 320 of the anterior translator 300 have advanced into the slots. The grooves 125, 126 may additionally contain tick marks or other indicia to help a surgeon more easily determine how far the extensions 315, 320 have advanced into the slots 120, 121. The grooves 125, 126 may also provide an amount of relief in the body 100. The apertures 130, 131 of the medial and lateral slots 120, 121 generally correspond to the apertures 325, 330 of the medial and lateral extensions 315, 320, such that anterior translator pins 350 can be inserted through the apertures of the slots and further into the apertures of the extensions, locking the anterior translator 300 in a desired position. In the illustrated embodiment, each slot 120, 121 includes two apertures 130, 131, while each extension 315, 320 includes two columns of multiple apertures 325, 330. This configuration allows the anterior translator 300 to be positioned in multiple locations in the anterior/posterior direction while staying in a mostly fixed position in the medial/lateral direction. The ability of the anterior translator 300 to translate in the anterior/posterior direction allows the anterior translator to contact the highest point on the anterior femur 20. This contact, in combination with the contact between the posterior feet 200, 205 and the femur 20, helps stabilize the femoral pin guide 10 on the femur.

The anterior translator 300 further includes two apertures 335 on the body 305. These apertures function to guide a drill for distal resection guide pins 355. The use of apertures 335 with distal resection guide pins 355 is described more fully below with reference to FIGS. 12-13. In the illustrated embodiment, there are two apertures 335 that generally correspond to the location of two apertures in a separate cutting guide. In other embodiments, the femoral pin guide 10 may include multiple sets of apertures 335, each set of apertures corresponding to a different type or model cutting guide, with each set of apertures 335 including indicia relating to which type or model cutting guide the particular set of apertures 335 corresponds.

The body 305 of the anterior translator 300 also includes an additional set of apertures 340. The additional apertures 340 function to accept an anterior arm pin 425 to connect the anterior arm 400 to the anterior translator 300. The anterior translator 300 may also include a slot or aperture 345. The slot or aperture 345 allows a surgeon to guide a cutting blade through the slot to perform the distal cut during an arthroplasty procedure, described more fully below with reference to FIGS. 13-15. The slot or aperture 345 may alternately be configured to allow access by any number of instruments such as pins. Further, the slot or aperture 345 may be fully omitted.

Figure 5:
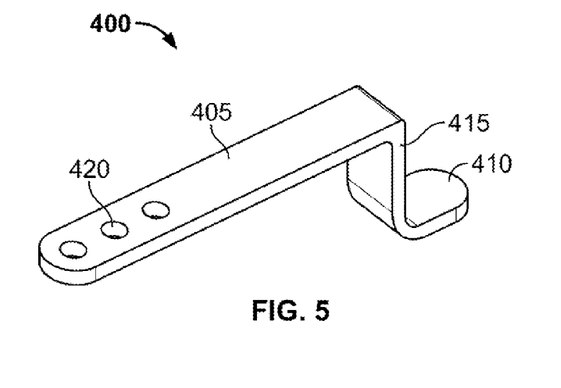
FIG. 5 is a perspective view of the anterior arm of FIG. 1.
Figure 12:
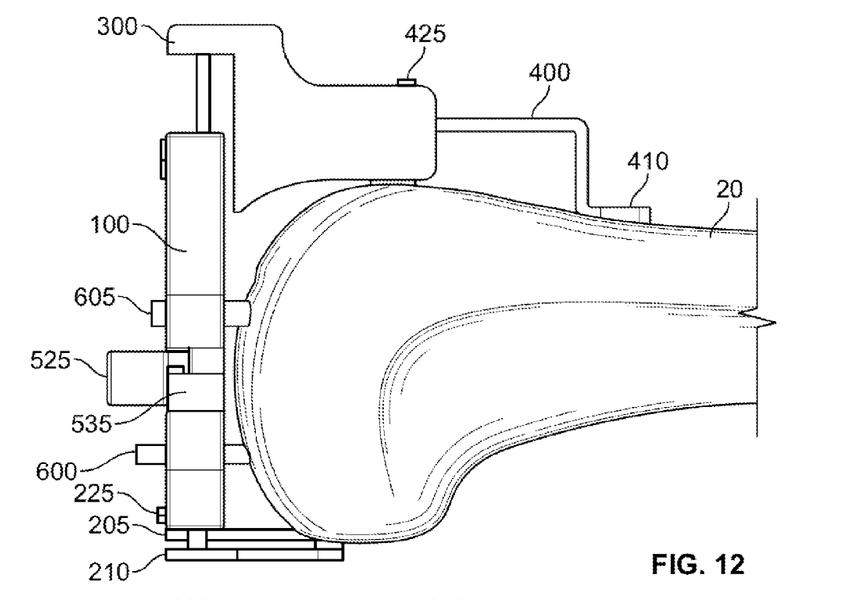
FIG. 12 is a side plan view of the femoral pin guide with the anterior arm positioned on the femur.
Figure 13:
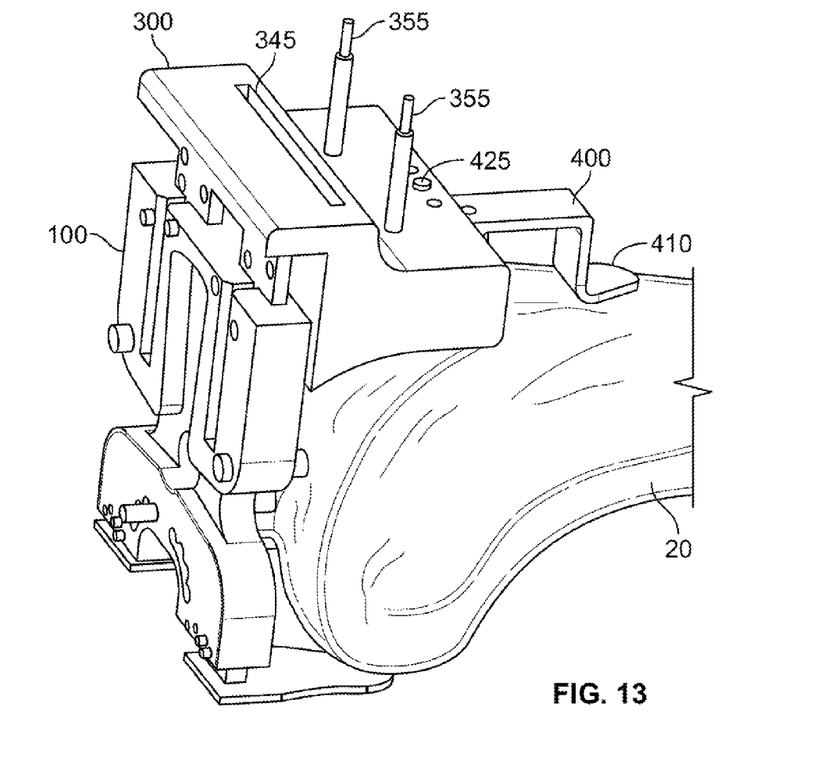
FIG. 13 is a perspective view of the femoral pin guide with the anterior arm positioned on the femur.

Referring to FIG. 5, an anterior arm 400 for use with the anterior translator 300 is shown. Generally, the anterior arm 400 includes a flat extension portion 405, a flat contact portion 410, and a transverse connection portion 415 that connects the two. The distal end of the extension portion 405 includes a plurality of apertures 420 extending through the extension portion. During the process of fitting the femoral pin guide 10 to the femur 20, the distal end of the extension 405 of the distal arm 400 is inserted into a slot in the proximal end of the body 305 of the anterior translator 300. One of the apertures 420 of the anterior arm 400 is aligned with one of the apertures 340 of the anterior translator 300, and an anterior arm pin 425 is inserted through each aperture to secure the anterior arm to the anterior translator. The configuration of apertures 340, 420 allows for the anterior arm 400 to be positioned in multiple medial/lateral and proximal/distal positions. The anterior translator 300 may also contain multiple slots in the anterior/posterior direction, such that the anterior arm 400 may have different possible positions in the anterior/posterior direction as well. Other mechanisms may also be utilized to provide for positioning of the anterior arm at different positions in the anterior/posterior direction. When the anterior arm 400 is coupled with the anterior translator 300, the contact portion 410 of the anterior arm contacts a surface on the anterior femur 20. Preferably, the contact is on the anterior cortex. The anterior arm 400, once in place, provides additional stability to the femoral pin guide 10 and more particularly provides a desired flexion/extension orientation of the femoral pin guide, as illustrated in FIGS. 12-13.

In one embodiment, the anterior translator 300 is used as the primary contact point for clamping and stability, while the anterior arm 400 is used to reference an anatomical point on the anterior femur. In this embodiment, the anterior translator 300 and anterior arm 400 are decoupled and move independently of each other, with the anterior arm capable of movement in the anterior/posterior, medial/lateral, and proximal/distal directions. In another embodiment, the anterior translator 300 and anterior arm 400 are combined into one arm that is capable of moving in the anterior/posterior, medial/lateral, and proximal/distal directions. The combined arm has the function of both clamping and referencing an anatomical point on the femur.

Figure 6:
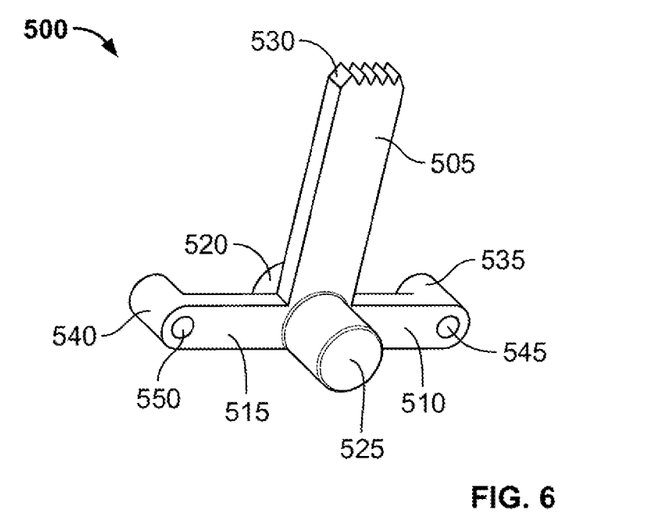
FIG. 6 is a perspective view of a rotation arm.

Referring to FIG. 6, the rotation arm 500 is shown. Generally, the rotation arm 500 includes a main body 505 and two extensions 510, 515 extending generally orthogonal to the main body. The rotation arm 500 also includes a generally cylindrical insert 520 on the proximal side of the rotation arm and a generally cylindrical handle 525 on the distal side of the rotation arm. Now referring to both FIGS. 2 and 6, the insert 520 is shaped to mate with the rotation arm aperture 150 of the body 100. As discussed above, the main body 505 fits within the rotation arm slot 155 of the body 100. A user can grip and manipulate the handle 525 of the rotation arm 500 to rotate the main body 505 and extensions 510, 515. The boundaries of the rotation arm slot 155 provide for a maximum amount of rotation in either direction.

Additionally, the main body 505 may include texturing, such as ridges 530 at the anterior end of the main body. Corresponding texturing, such as mating ridges, may also be included at the anterior boundary of the rotation arm slot 155 in the body 100 (texturing not illustrated in FIG. 2). The interaction between ridges 530 of the rotation arm 500 and complementary ridges of the body 100 provides for locking of the rotational position in discrete stages. The ridges 530 may be configured such that, once inserted, the rotation arm is locked into a rotational position. The ridges 530 may alternative be configured such that, once inserted, the rotation arm may be discretely rotated in a clicking fashion if enough force is applied to overcome the friction provided by the ridges 530. As the rotation arm 500 rotates, the extension arms 510, 515 also rotate to position drill guides 535, 540 at a desired orientation. Once at the desired orientation, a surgeon can drill into the femur through apertures 545, 550 in the drill guides 535, 540. This drilling functions to provide points in the femur 20 for attachment of a device, such as a 4-in-1 cutting block, to make cuts into the femur. This is described more fully below with reference to FIGS. 14-15. It should be recognized that other means could be employed to secure the orientation of the rotation arm.

In an arthroplasty procedure using the femoral pin guide 10, following the imaging of a knee and related steps described above, a surgeon can obtain a set of coordinates for the femoral pin guide that instruct guide assembly that provides specific positioning of the guide on that femur. The coordinates generally correspond to different positions of the various subsystems described above in relation to the body 100 and anterior translator 300 of the femoral pin guide 10.

Figure 7:
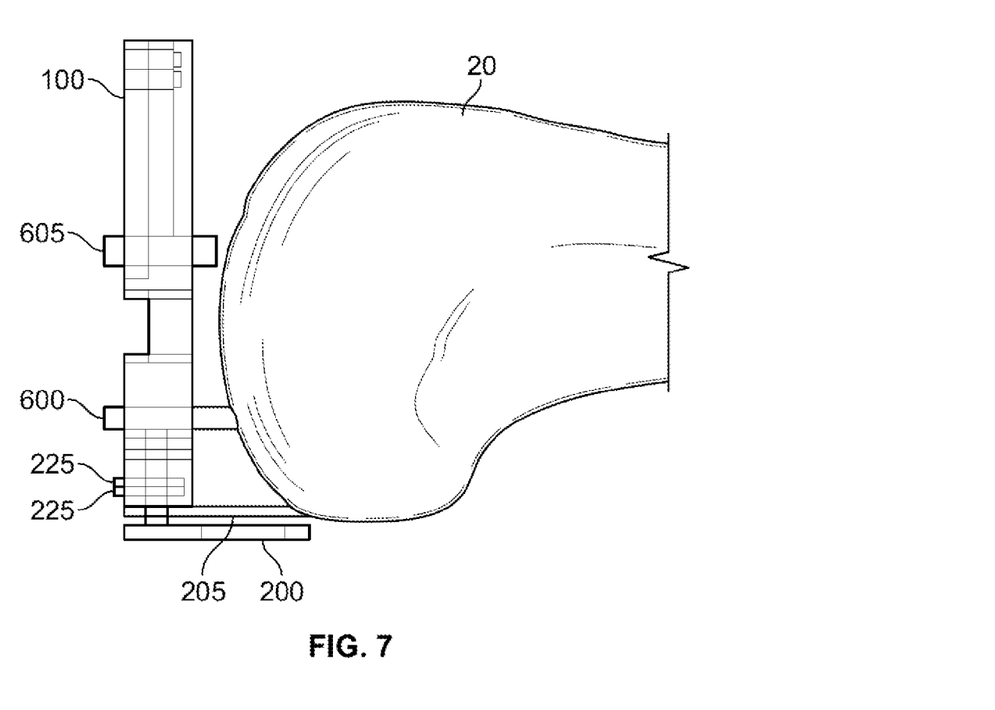
FIG. 7 is a side plan view in partial phantom lines of the body and posterior feet of the femoral pin guide positioned on the femur.
Figure 8:
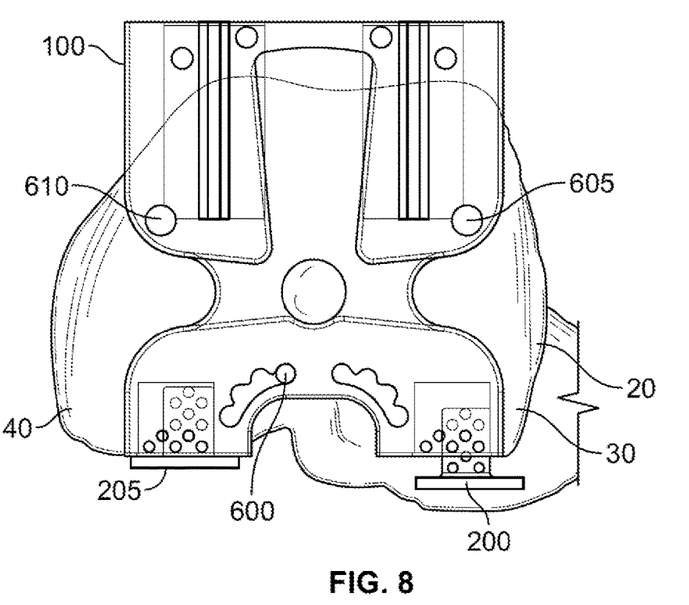
FIG. 8 is a front plan view in partial phantom lines of the body and posterior feet of the femoral pin guide positioned on the femur.
Figure 9:
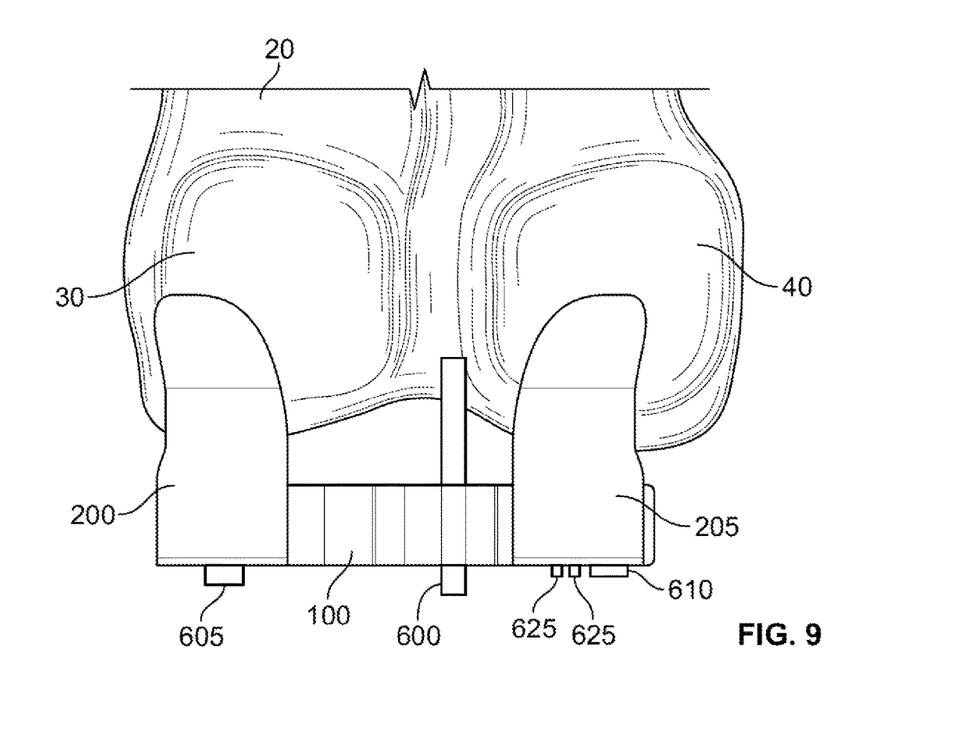
FIG. 9 is a bottom plan view in partial phantom lines of the body and posterior feet of the femoral pin guide positioned on the femur.

In the illustrated embodiment, the coordinates are locations of pins within the different apertures described above. The coordinates also include a rotational position of the rotation arm 500, for example the angle of the rotation arm. As shown in FIGS. 7-9, two posterior foot pins 225 are inserted into apertures 115 of the medial extension 105 of the body 100 and through apertures 220 in the medial posterior foot 200. An additional two posterior foot pins 225 are inserted into the apertures 116 of the lateral extension 106 of the body 100 and through apertures 220 in the lateral posterior foot 205. Each group of two posterior foot pins 225 securely positions the posterior feet 200, 205 in the desired location. An intercondylar notch pin 600 is inserted into one of the plurality of medial and lateral apertures 140, 141 in the body 10 of the pin guide. A medial condyle pin 605 is inserted into the medial aperture 135 of the body 100 and a lateral condyle pin 610 is inserted into the lateral aperture 136 of the body.

Once the pins are inserted, as shown in FIGS. 7-9 (posterior foot pins 225 not shown in FIG. 8), the surgeon slides medial posterior foot 200 under the medial condyle 30 and the lateral posterior foot 205 under the lateral condyle 40. The surgeon slides the body 100 until the intercondylar notch pin 600 contacts either the medial condyle 30 or the lateral condyle 40, as best seen in FIGS. 8 and 9, as prescribed by the guide coordinates. The surgeon further positions the body 100 such that the medial and lateral condyle pins 605, 610 both contact the respective condyles 30, 40. At this point, both posterior feet 205, 210, the intercondylar notch pin 600, and the medial and lateral condyle pins 605, 610 all are in contact with the femur. The posterior feet 205, 210 help set the anterior/posterior location of the drill guides 535, 540 of the rotation arm 500. The medial and lateral condyle pins 605, 610 help to set the varus/valgus angle of the distal cut.

Figure 10:
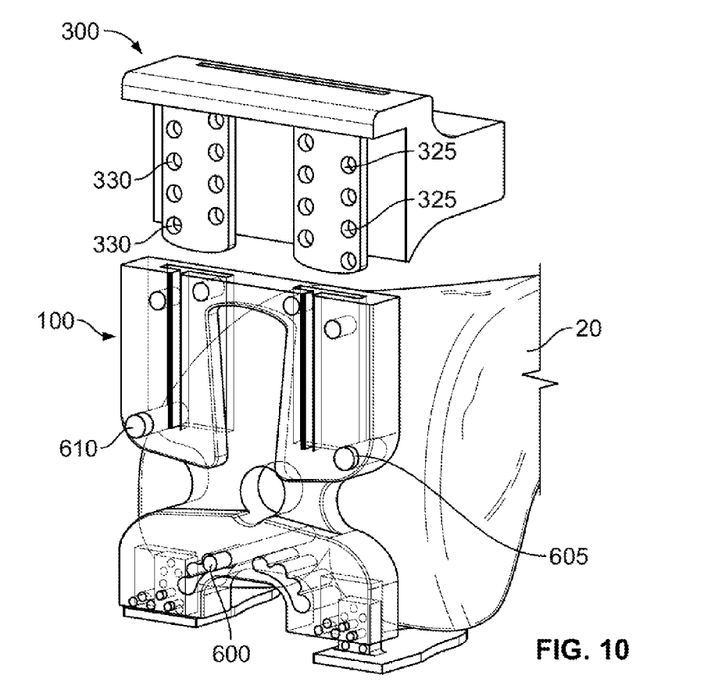
FIG. 10 is an exploded perspective view in partial phantom lines of the anterior translator and the body of the femoral pin guide.
Figure 11:
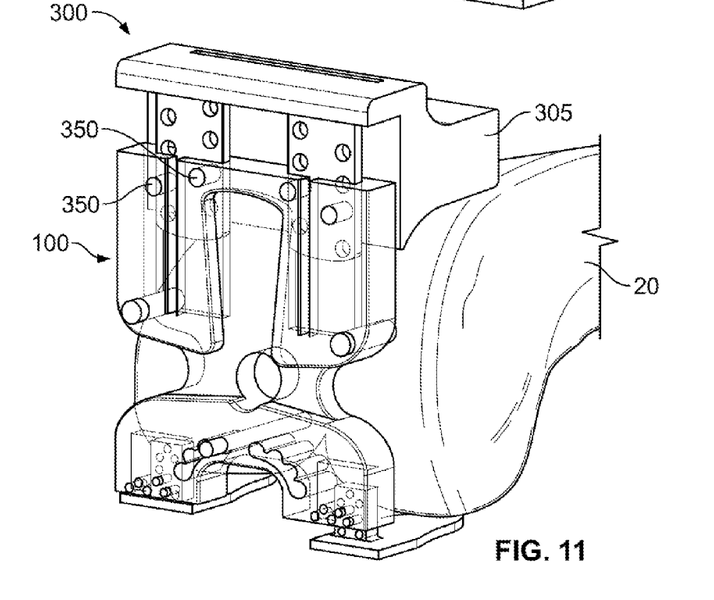
FIG. 11 is a perspective view in partial phantom lines of the anterior translator coupled to the body of the femoral pin guide.

Referring generally to FIGS. 10-11, the anterior translator 300 is shown before and after insertion into the body 100, respectively. The medial and lateral extensions 315, 320 of the anterior translator 300 are inserted into the corresponding slots 120, 121 of the body 100. Anterior translator pins 350 are inserted into each of the two apertures 131 in the body 100 and further through two apertures 330 of the lateral extension 320 as prescribed by the guide coordinates. An additional two anterior translator pins 350 are also inserted to secure the medial extension 315 of the anterior translator 300 (pins 350 not illustrated for medial extension 315 in FIG. 11). In this position, the posterior side of the body 305 of the anterior translator 310 contacts the anterior surface of the femur 20, providing support to the femoral pin guide 10.

Referring generally to FIGS. 12-13, the anterior arm 400 is inserted into a slot in the proximal side of the anterior translator (not shown) such that the desired anterior arm aperture 420, as dictated by the guide coordinates, aligns with the desired anterior translator aperture 340. Once aligned, the surgeon inserts an anterior arm pin 425 through both the anterior arm aperture 420 and the anterior translator aperture 340. This fixes the anterior/posterior and medial/lateral position of the anterior arm 400 with respect to the anterior translator 300. The contact portion 410 of the anterior arm 400 contacts the anterior cortex of the femur 20. This element of the guide provides for the flexion/extension orientation of the femoral pin guide 10 with respect to the femur 20. Once the guide is fully assembled and in place on the femur, the surgeon drills through guide apertures 335 into the femur and inserts two distal resection guide pins 355 through the two apertures 335 in the body 305 of the anterior translator 300. These pins provide increased stability to the femoral guide 10 during the distal cut, described in more detail below with respect to FIGS. 14-15, or direct the placement of a separate distal cutting block.

Figure 14:
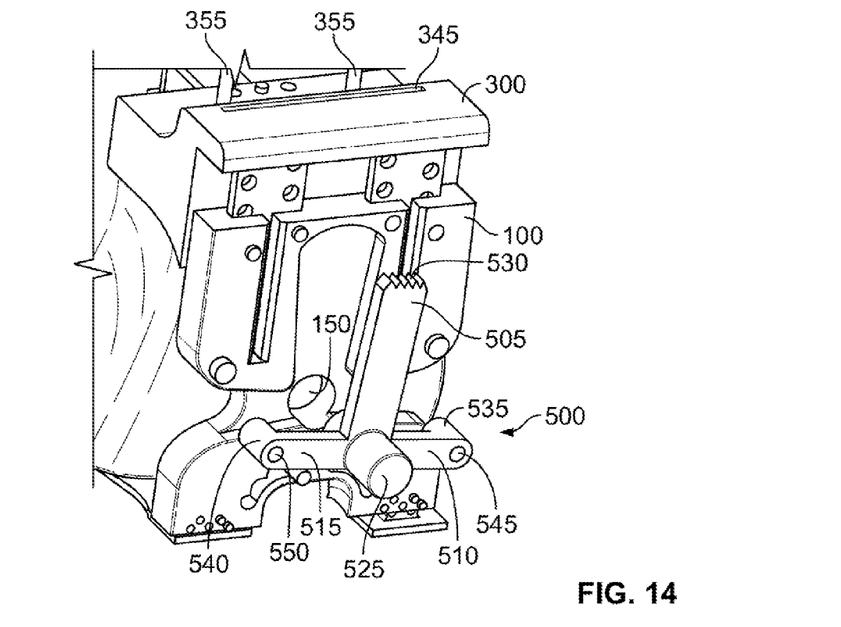
FIG. 14 is an exploded perspective view of the rotation arm and the femoral pin guide.
Figure 15:
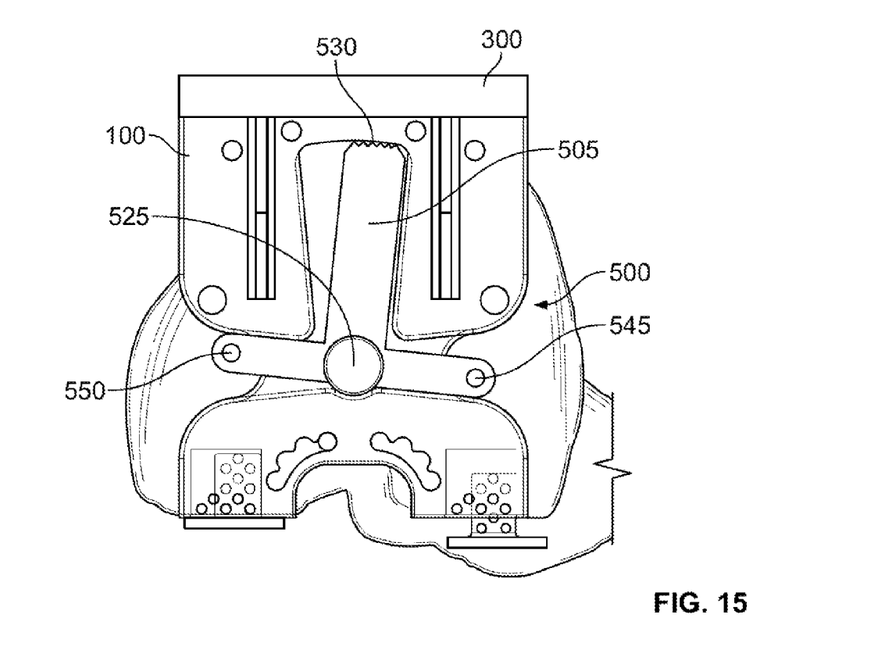
FIG. 15 is a front plan view of the femoral pin guide with the rotation arm coupled to the femoral pin guide.

Referring generally to FIGS. 14-15, the rotation arm 500 is illustrated before and after being coupled to the body 100, respectively. As described above with reference to FIG. 5, and as illustrated best in FIG. 14, the surgeon aligns the main body 505 of the rotation arm 500 with the rotation arm slot 155 of the body 100. Using the handle 525 of the rotation arm 500, the surgeon presses the cylindrical insert 520 into the rotation arm aperture 150 of the body 100 to couple the rotation arm to the body at a predetermined angle. The ridges 530 on the anterior end of the main body make contact with a corresponding texturized surface in the rotation arm slot 155 to restrict unintentional rotation of the rotation arm 500. The rotation arm 500 sets the internal/external rotation of the pin holes for an additional device, such as a 4-in-1 cutting block. Once the rotation arm 500 is in the desired position, the surgeon drills into the femur 20 using the drill guides 545, 550 on the extensions 510, 515. These drill holes in the femur 20 provide a location for an additional device, such as a 4-in-1 cutting block, to make the additional cuts (e.g. (i) anterior cut, (ii) posterior cut, (iii) anterior chamfer cut, and (iv) posterior chamfer cut) after the distal cut is made.

After drilling the holes into the femur 20 using the rotation arm 500 as a guide, the surgeon can perform the distal cut on the femur 20. If using an embodiment of the femoral pin guide 10 in which the anterior translator 300 does not have a slot or aperture 345, the surgeon removes the femoral pin guide and couples a distal cutting guide to the femur by aligning apertures in the distal cutting guide with distal resection guide pins 355. The distal cut is made using the separate distal cutting guide. To perform the distal cut using an embodiment of the femoral pin guide 10 that includes an anterior translator 300 with a slot or aperture 345, the surgeon inserts a tool, such as a reciprocating blade, through the slot 345 of the anterior translator 300. The slot 345 provides guidance for a flat cut.

Once the distal cut is made, the holes in the femur 20 drilled through the rotation arm 500 will be deep enough to still be visible. At this point, the surgeon can remove and/or disassemble the femoral pin guide 10, if not already removed. After the femoral pin guide 10 is removed, the surgeon can couple an additional device (not shown), such as a 4-in-1 cutting block, to the flat surface of the femur 20, positioned by additional pins (not illustrated) in the previously drilled holes. The surgeon may perform the remaining cuts and couple one or more implants to the bone, as is known in the art.

The femoral pin guide 10 has been described and illustrated with specific numbers of apertures for pins in different subsystems. For example, the posterior feet 200, 205 are each illustrated with three columns of three apertures 220, for a total of nine apertures. Each extension 315, 320 is illustrated with two columns of four apertures 325, 330, for a total of eight apertures each. It should be understood that the specific number and arrangement of apertures for all of the subsystems described above may be altered from the illustrated embodiment, and such alteration is largely a matter of design choice.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adjustable guide comprising:
a body having a plurality of apertures, at least one of the apertures configured to receive a pin having a contact surface configured to contact a distal portion of the femur;
an anterior adjustment member couplable to an anterior portion of the body in an anterior/posterior direction in a plurality of positions, the anterior adjustment member having an inner contact surface configured to contact an anterior portion of the femur;
a medial posterior foot couplable to a medial extension a posterior portion of the body in the anterior/posterior direction in a plurality of positions, the medial posterior foot having an inner contact surface, a posterior portion of the inner contact surface of the medial posterior foot configured to contact a medial condyle of the femur; and
a lateral posterior foot couplable to a lateral extension of the posterior portion of the body in the anterior/posterior direction in a plurality of positions, the lateral posterior foot having an inner contact surface, a posterior portion of the inner contact surface of the lateral posterior foot configured to contact a lateral condyle of the femur;
a plurality of apertures in the medial extension and a plurality of apertures in the medial posterior foot, the apertures in the medial extension configured to align with the apertures in the medial posterior foot and to accept a medial foot fastener therethrough; and
a plurality of apertures in the lateral extension and a plurality of apertures in the lateral posterior foot, the apertures in the lateral extension configured to align with the apertures in the lateral posterior foot and to accept a lateral foot fastener therethrough,
wherein the coupled positions of the body, the anterior adjustment member, the medial posterior foot, and the lateral posterior foot, with respect to one another affect a position of the at least one of the plurality of apertures of the body in relation to the femur.

2. The adjustable guide of claim 1, wherein the plurality of apertures in the medial extension and the plurality of apertures in the medial posterior foot are arranged such that the medial posterior foot is capable of being fastened to the medial extension in at least two discrete positions in a medial/lateral direction and in at least two discrete positions in the anterior/posterior direction.

3. The adjustable guide of claim 2, wherein the plurality of apertures in the lateral extension and the plurality of apertures in the lateral posterior foot are arranged such that the lateral posterior foot is capable of being fastened to the lateral extension in at least two discrete positions in the medial/lateral direction and in at least two discrete positions in the anterior/posterior direction.

4. The adjustable guide of claim 1, wherein the anterior adjustment member further comprises a first extension including a plurality of apertures, each of the plurality of apertures in the first extension configured to align with at least one of the plurality of apertures in the body and to accept a first extension fastener therethrough.

5. The adjustable guide of claim 4, wherein the plurality of apertures in the first extension and the plurality of apertures in the body are arranged such that the first extension is capable of being fastened to the body in at least two discrete positions in the anterior/posterior direction.

6. The adjustable guide of claim 5, wherein the anterior adjustment member further comprises a second extension including a plurality of apertures, each of the plurality of apertures in the second extension configured to align with at least one of the plurality of apertures in the body and to accept a second extension fastener therethrough.

7. The adjustable guide of claim 6, wherein the plurality of apertures in the second extension and the plurality of apertures in the body are arranged such that the second extension is capable of being fastened to the body in at least two discrete positions in the anterior/posterior direction.

8. The adjustable guide of claim 1, wherein the anterior adjustment member includes at least two drill guide apertures in the anterior adjustment member configured to guide a drill.

9. The guide of claim 8, wherein the drill guide apertures are adapted to be used to create recesses in the bone with a cutting tool, the recesses adapted to be created using the drill guide apertures corresponding with fixation posts of a distal resection cutting guide.

10. The adjustable guide of claim 1, further including an anterior arm couplable to a proximal portion of the anterior adjustment member, the anterior arm including a bone contacting portion configured to contact the femur proximal of the anterior adjustment member,
wherein the anterior adjustment member further includes a plurality of proximal apertures, each of the plurality of proximal apertures configured to align with at least one of a plurality of apertures in the anterior arm, each of the plurality of proximal apertures being capable of accepting an anterior arm fastener therethrough.

11. The adjustable guide of claim 10, wherein the plurality of proximal apertures and the plurality of apertures in the anterior arm are arranged such that the anterior arm is capable of being fastened to the anterior adjustment member in at least two discrete positions in a medial/lateral direction and in at least two discrete positions in a proximal/distal direction.

12. The adjustable guide of claim 1 further comprising a rotation arm configured to be coupled to a distal portion of the body, the rotation arm including at least two guide members extending in a medial/lateral direction, each guide member being configured to accept at least one of a pin or a drill.

13. The adjustable guide of claim 12, wherein the body includes a rotation arm recess with a medial side, a lateral side, and an anterior side, the rotation arm recess configured to accept at least a portion of the rotation arm therein.

14. The adjustable guide of claim 13, wherein the anterior side of the rotation arm recess includes a textured surface and further wherein an anterior portion of the rotation arm includes a textured surface, the textured surface of the recess configured to contact the textured surface of the rotation arm when the rotation arm is coupled to the body.

15. An adjustable guide comprising:
a body having a plurality of apertures, at least one of the apertures configured to receive a pin having a contact surface configured to contact a distal portion of the femur;
an anterior adjustment member couplable to an anterior portion of the body in an anterior/posterior direction in a plurality of positions, the anterior adjustment member having an inner contact surface configured to contact an anterior portion of the femur;

at least one posterior foot couplable to a posterior portion of the body in the anterior/posterior direction in a plurality of positions, the at least one posterior foot having an inner contact surface configured to contact a posterior portion of the femur; and an anterior arm couplable to a proximal portion of the anterior adjustment member, the anterior arm including a bone contacting portion configured to contact the femur proximal of the anterior adjustment member, wherein the anterior adjustment member further includes a plurality of proximal apertures, each of the plurality of proximal apertures configured to align with at least one of a plurality of apertures in the anterior arm, each of the plurality of proximal apertures being capable of accepting an anterior arm fastener therethrough, wherein the coupled positions of the body, the anterior adjustment member, and the at least one posterior foot, with respect to one another affect a position of the at least one of the plurality of apertures of the body in relation to the femur.

16. The adjustable guide of claim 15, wherein the plurality of proximal apertures and the plurality of apertures in the anterior arm are arranged such that the anterior arm is capable of being fastened to the anterior adjustment member in at least two discrete positions in a medial/lateral direction and in at least two discrete positions in a proximal/distal direction.

17. An adjustable guide comprising:
a body having a plurality of apertures, at least one of the apertures configured to receive a pin having a contact surface configured to contact a distal portion of the femur;

an anterior adjustment member couplable to an anterior portion of the body in an anterior/posterior direction in a plurality of positions, the anterior adjustment member having an inner contact surface configured to contact an anterior portion of the femur;

at least one posterior foot couplable to a posterior portion of the body in the anterior/posterior direction in a plurality of positions, the at least one posterior foot having an inner contact surface configured to contact a posterior portion of the femur; and a rotation arm configured to be coupled to a distal portion of the body, the rotation arm including at least two guide members extending in a medial/lateral direction, each guide member being configured to accept at least one of a pin or a drill;

wherein the coupled positions of the body, the anterior adjustment member, and the at least one posterior foot, with respect to one another affect a position of the at least one of the plurality of apertures of the body in relation to the femur.

18. The adjustable guide of claim 17, wherein the body includes a rotation arm recess with a medial side, a lateral side, and an anterior side, the rotation arm recess configured to accept at least a portion of the rotation arm therein.

19. The adjustable guide of claim 18, wherein the anterior side of the rotation arm recess includes a textured surface and further wherein an anterior portion of the rotation arm includes a textured surface, the textured surface of the recess configured to contact the textured surface of the rotation arm when the rotation arm is coupled to the body.

* * * * *